March 17, 1964 A. MEILLAND Plant Pat. 2,378
ROSE PLANT
Filed April 9, 1963
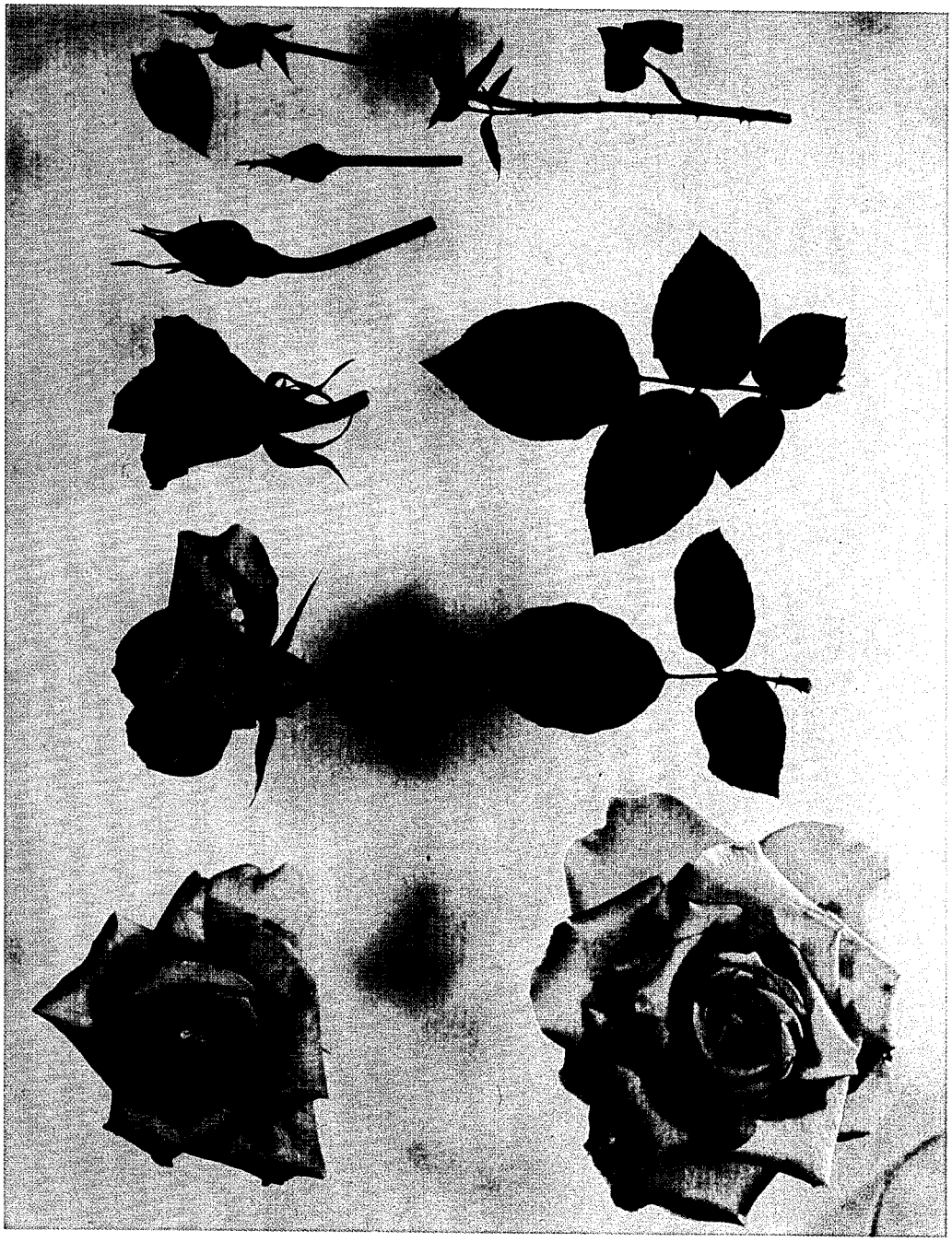
Inventor.
Alain Meilland
By: Robb & Robb
Attorneys.

United States Patent Office

Plant Pat. 2,378
Patented Mar. 17, 1964

2,378
ROSE PLANT

Alain Meilland, Alpes Maritimes, France, assignor to The Conard-Pyle Company, West Grove, Pa., a corporation of Pennsylvania Filed Apr. 9, 1963, Ser. No. 271,819
Claims priority, application France Sept. 7, 1962
1 Claim. (Cl. Plt.—11)

The present invention relates to a new and distinct variety of rose plant of the hybrid tea class, which was originated by me by crossing the variety "White Knight" (U.S. Plant Patent No. 1,359), known in Europe as "Message," with an unnamed and unpatented seedling derived from a cross of "Happiness" (U.S. Plant Patent No. 911), known in France as "Rouge Meilland," × "Independence (U.S. Plant Patent No. 1,036), known in Germany as "Kordes' Sondermeldung."

The primary objective of this breeding was to produce a new and improved rose variety that is especially suitable for the production of cut flowers when grown under glass, and which bears flowers of double form and a pink general color tonality, while at the same time being less sensitive to damp weather which tends to deteriorate the first petals and then causes the flowers to "ball" and lose their true color, and still further having the ability to produce flowers in great abundance and of good quality even during the summer season when the quality normally tends to decrease because of thinner petalage at that time of year. This objective was fully achieved, along with other desirable improvements, as evidenced by the following unique combination of characteristics which are outstanding in the new variety and which distinguish it from its parents, as well as from all other varieties of which I am aware:

(1) A vigorous habit of growth and superior flower productivity when grown under glass for commercial cut-flower production;

(2) A habit of bearing the flowers on strong and heavy necks;

(3) An excellent and very double flower form, combined with a slow-opening habit and retention of the flower form throughout the life of the blooms;

(4) Good flower petalage, usually ranging from 35 to 40 petals, combined with a strong petal substance;

(5) A distinctive and attractive general color tonality of the flowers corresponding to Rhodamine Pink; and (6) A superior cut-flower longevity when kept under ordinary living room conditions, averaging at least three days longer than such well-known varieties as "Better Times" (U.S. Plant Patent No. 23) and "Golden Rapture" (unpatented).

In comparison with its seed parent, "White Knight," the habit of growth of the new variety is more vigorous and stronger; the new variety is especially suited for greenhouse cut-flower forcing, as distinguished from the parent variety which does not perform well under these conditions; the flowers of the new variety have improved substance and are much longer lasting when cut for indoor decoration; and the general color effect of the flowers of the new variety is Rhodamine Pink in contrast with the pure white flowers of "White Knight."

As compared with the unnamed seedling parent, which was the pollen parent of the new variety, the new variety is much superior in its suitablity for green house cut-flower production; it has a substantially better flower form, and the flowers have a longer life when used as cut flowers indoors.

Asexual reproduction of the new variety by budding, as performed in France, and also at London Grove, Pennsylvania, U.S.A., shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with the Horticultural Colour Chart of the Royal Horticultural Society, except where general color terms of ordinary dictionary significance are obvious:

Type: Hardy; bush; greenhouse and outdoor; seedling; for cut flowers and for garden decoration.
Class: Hybrid tea.
Breeding: Seedling.
*Seed parent.*—"White Knight."
*Pollen parent.*—An unnamed seedling of "Happiness" × "Independence."
Propagation: Holds its distinguishing characteristics through succeeding propagations by budding.

*Flower*

Locality where grown and observed: London Grove, Pennsylvania, U.S.A.
Flowers borne: Singly to stem; on strong, long stems.
Quantity of bloom: Free, in greenhouse.
Continuity: Continuous.
Fragrance: Moderate. Nature—tea.
Bud:
*Peduncle.*—Long; medium heavy; erect; stiff; almost smooth; with few green prickles. Color—Lettuce Green, Plate 861.
*Before calyx breaks.*—Size—medium. Form—pointed; ovoid; with a conspicuous neck; with foliaceous appendages on the surface of the bud; with slender, entire foliaceous parts extending beyond the tip of the bud equal to ½ or more of its length.
*As calyx breaks.*—Color—Tyrian Purple, Plate 727.
*As first pedal opens.*—Size—medium. Form—long; ovoid. Color: outside—near Rose Red, Plate 724/1, washed with near Solferino Purple, Plate 26/1, with point of attachment Sap Green, Plate 62/3; inside—near Spinel Pink, Plate 0625/1, washed with Spinel Pink, Plate 0625 toward margin of petal, with point of attachment Sap Green, Plate 62/3.
*Opening.*—Opens up well.
Bloom:
*Size (when fully open).*—Large; from 5 inches to 5½ inches.
*Petalage.*—Very double; from 35 to 40 petals; arranged regularly.
*Form.*—High-centered at first, and remaining high-centered; petals being at first loosely rolled outward, but later becoming tightly rolled outward at maturity.
Petals:
*Texture.*—Medium thickness; leathery.
*Appearance.*—Inside—satiny. Outside—shiny.
*Shape.*—Outer petals—usually round. Intermediate petals—round. Inner petals—obovate.

This description of a newly opened flower was made from a rose grown in a greenhouse during the month of April at London Grove, Pennsylvania, U.S.A.:

*Color.*—Outer petal: outside surface—Rose Bengal, Plate 25/2, shading to near China Rose, Plate 024 over basal ¼ of petal, with point of attachment Sap Green, Plate 62/3; inside surface—between Rhodamine Pink, Plate 527/1 and Rhodamine Pink, Plate 527/2, with small area of Rose Bengal, Plate 25/2 adjoining lower margin, and with point of attachment Sap Green, Plate 62/3. Intermediate petal: outside surface—Rose Bengal, Plate 25/2, shading to near China Rose, Plate 024 over basal ¼ of petal, with point of attachment Sap Green, Plate 64/3; inside surface—near Rhodamine Pink, Plate 527/1, margined with Rose Bengal, Plate 25/2 over basal ¼ of petal, with point of attachment Sap Green, Plate 62/3. Inner petal: outside surface—near Rose Bengal, Plate 25/1, with point of attachment Sap Green, Plate 62/3; inside surface—Neyron Rose, Plate 623/2, with point of attachment Sap Green, Plate 62/3.

This description was made from a rose that was open for three days in a greenhouse during the month of January at London Grove, Pennsylvania, U.S.A.:

*Color.*—Outer petal: outside surface—Fuchsine Pink, Plate 627/2, irregularly blotched with Fuchsine Pink, Plate 627/3 and broadly margined with Fuchsine Pink, Plate 627/1, and with point of attachment near white; inside surface—Fuchsine Pink, Plate 627/3, with point of attachment near Sap Green, Plate 62/3. Inner petal: outside surface—Rhodamine Pink, Plate 527, with point of attachment near white; inside surface—Rhodamine Pink, Plate 527/1, with a streak of near white running up the midrib, and with point of attachment Sap Green, Plate 62/3.

*General color effect.*—Newly opened flower— Rhodamine Pink, Plate 527. 3-days open—Rhodamine Pink, Plate 527.

*Behavior.*—Persist.

*Flower longevity.*—Cut roses grown in greenhouse and kept at living room temperatures—6 days in January.

*Reproductive Organs*

Stamens: Many; arranged irregularly about pistils; mixed with petaloids.

Filaments: Medium length; most with anthers. Color—near Magenta, Plate 27/3.

Anthers: Medium size; open at various times; occasionally an anther fused with a petaloid. Color—near Indian Yellow, Plate 6/1.

Pollen: Moderate quantity. Color—gold.

Pistils: Medium number.

Styles: Uneven; medium length; medium heaviness; bunched.

Stigma: Color—white-yellow.

Ovaries: Usually all enclosed in receptacle.

Hips: None observed.

Sepals: Permanent; moderately long; spear-shaped.

Seeds: None observed.

*Plant*

Foliage:

*Leaves.*—Compound of 3, 5 or occasionally 7 leaflets; normal abundance; moderately large, leathery.

*Leaflets.*—Shape—oval, with apex acute. Base—obtuse. Margin—simply serrate.

*Color.*—Mature: upper surface—near Spinach Green, Plate 0960; under surface—Lavender Green, Plate 000761. Young: upper surface—near Fern Green, Plate 0862, overlaid with Oxblood Red, Plate 00823; under surface—Willow Green, Plate 000862/1, overlaid with near Erythrite Red, Plate 0027.

*Rachis (the supporting stem of the compound leaf).*—Medium size. Upper side—grooved; hairy. Under side—sparsely prickly.

*Stipules.*—Medium length; narrow; with points of medium length turning out at an angle of 45°.

*Disease resistance.*—Comparable to that of the average variety grown under the same cultural conditions at London Grove, Pennsylvania, U.S.A.

Growth:

*Habit.*—Bushy; upright; much-branched.

*Growth.*—Free.

*Canes.*—From medium caliper to heavy.

*Main Stems.*—Dull. Color—Lettuce Green, Plate 861. Prickles—several; color—somewhat lighter than Garnet Brown, Plate 00918/3. Hairs—none.

*Branches.*—Bright. Color—Lettuce Green, Plate 861. Prickles—several; color—flesh color. Hairs—none.

*New shoots.*—Bright. Color—Lettuce Green, Plate 861/1. Prickles—several; color—Fern Green, Plate 0862/3. Hairs—none.

I claim:

A new and distinct variety of rose plant of the hybrid tea class, substantially as herein shown and described, characterized particularly as to novelty by the unique combination of a vigorous habit of growth and superior flower productivity when grown in a greenhouse for cut-flower production, a habit of bearing the flowers on strong and heavy necks, an excellent flower form and slow-opening habit, said flowers maintaining their form throughout the life of the blooms, good flower petalage and strong petal abundance, a distinctive and attractive Rhodamine Pink general color tonality of the flowers, and superior flower longevity as cut flowers when kept under living room conditions.

No references cited.